(12) United States Patent
Gratacap et al.

(10) Patent No.: US 12,123,000 B2
(45) Date of Patent: Oct. 22, 2024

(54) USE OF PI3KC2B INHIBITORS FOR THE PRESERVATION OF VASCULAR ENDOTHELIAL CELL BARRIER INTEGRITY

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); UNIVERSITY COLLEGE LONDON, London (GB); CENTRE HOSPITALIER UNIVERSITAIRE DE TOULOUSE, Toulouse (FR); UNIVERSITÉ DE CAEN NORMANDIE, Caen (FR); CENTRE HOSPITALIER RÉGIONAL UNIVERSITAIRE DE CAEN, Caen (FR)

(72) Inventors: Marie-Pierre Gratacap, Toulouse (FR); Jean Darcourt, Toulouse (FR); Bart Vanhaesebroeck, London (GB); Gaëtan Chicanne, Toulouse (FR);

(Continued)

(73) Assignees: INSERM (INSTITUT NATIONAL DE LA SANTE ET DE LA RECHERCHE MEDICALE), Paris (FR); UNIVERSITE PAUL SABATIER TOULOUSE III, Toulouse (FR); UNIVERSITY COLLEGE LONDON, London (GB); CENTRE HOSPITALIER UNIVERSITAIRE DE TOULOUSE, Toulouse (FR); UNIVERSITE DE CAEN NORMANDIE, Caen (FR); CENTRE HOSPITALIER REGIONAL UNIVERSITAIRE DE CAEN, Caen (FR)

( * ) Notice: Subject to any disclaimer, the term of this patent is extended or adjusted under 35 U.S.C. 154(b) by 407 days.

(21) Appl. No.: 16/972,152

(22) PCT Filed: Jun. 14, 2019

(86) PCT No.: PCT/EP2019/065694
§ 371 (c)(1),
(2) Date: Dec. 4, 2020

(87) PCT Pub. No.: WO2019/238933
PCT Pub. Date: Dec. 19, 2019

(65) Prior Publication Data
US 2021/0238605 A1 Aug. 5, 2021

(30) Foreign Application Priority Data
Jun. 15, 2018 (EP) .................................... 18305735

(51) Int. Cl.
*A61K 31/00* (2006.01)
*A61P 9/10* (2006.01)
(Continued)

(52) U.S. Cl.
CPC ............ *C12N 15/1137* (2013.01); *A61P 9/10* (2018.01); *G01N 33/5064* (2013.01); *C12N 2310/14* (2013.01); *C12N 2310/531* (2013.01)

(58) Field of Classification Search
CPC ......... A61K 31/00; G01N 2333/91215; G01N 33/5064; A61P 9/10; C12N 2310/14; C12N 2310/531
See application file for complete search history.

(56) References Cited

FOREIGN PATENT DOCUMENTS

| EP | 2 508 184 A1 | 10/2012 |
|---|---|---|
| WO | 2007/079999 A2 | 7/2007 |

(Continued)

OTHER PUBLICATIONS

Boller et al. (Anticancer Research, 2012 vol. 32:3015-3028).*
(Continued)

*Primary Examiner* — Terra C Gibbs
(74) *Attorney, Agent, or Firm* — WCF IP

(57) ABSTRACT

Ischemic conditions are a leading cause of death for both men and women. Ischemia, a condition characterized by
(Continued)

Figures 1A, 1B:
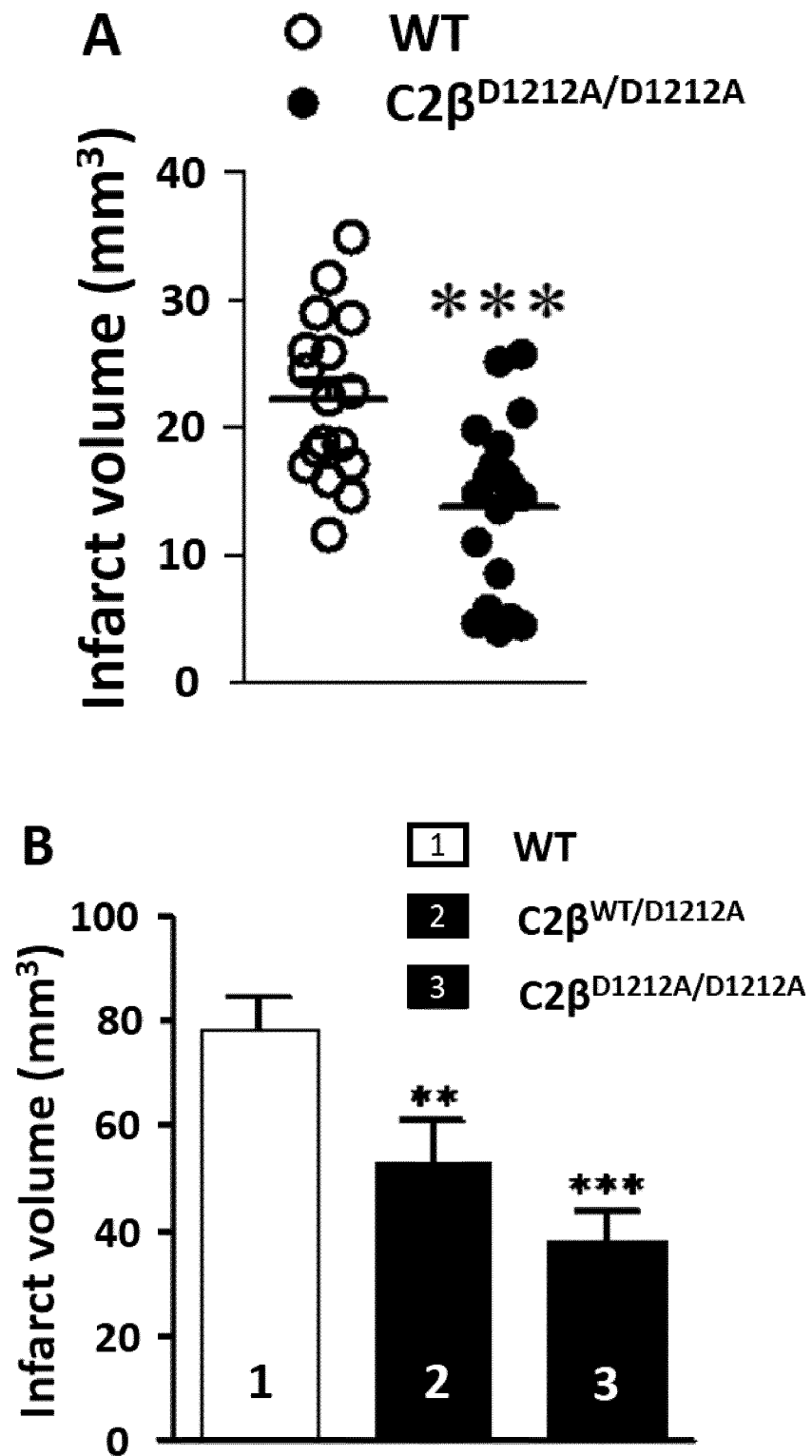

reduced blood flow and oxygen to an organ. Re-establishment of blood flow, or reperfusion, and re-oxygenation of the affected area following an ischemic episode is critical to limit irreversible damage. However, reperfusion also associates potentially damaging consequences. For instance, increased vascular permeability is an important contributor to edema and tissue damage following ischemic events. Here the inventors shows that genetic inhibition of PI3K-C2β reduces cerebral infarction in two ischemia/reperfusion (I/R) models and improves neurological outcome. The genetic inhibition stabilizes the blood-brain barrier (BBB) after ischemic stroke and reduces inflammation. Accordingly, the present invention relates to a method for the preservation of vascular endothelial cell barrier integrity in a patient in need thereof comprising administering to the subject a therapeutically effective amount of a PI3KC2β inhibitor.

5 Claims, 9 Drawing Sheets

Specification includes a Sequence Listing.

(72) Inventors: Bernard Payrastre, Toulouse (FR); Vincent Larrue, Toulouse (FR); Romain Solinhac, Toulouse (FR); Aude Jaffre, Toulouse (FR); Denis Vivien, Caen (FR); Typhaine Anquetil, Toulouse (FR)

(51) Int. Cl.
*C12N 15/113* (2010.01)
*G01N 33/50* (2006.01)

(56) References Cited

FOREIGN PATENT DOCUMENTS

| WO | 2008/025821 A1 | 3/2008 |
| WO | 2010/133534 A1 | 11/2010 |
| WO | 2012/122383 A2 | 9/2012 |
| WO | 2012/135166 A1 | 10/2012 |
| WO | 2014/068070 A1 | 5/2014 |

OTHER PUBLICATIONS

Tibolla et al., PLoS One. 2013; 8(1): e53808.*
Chikh et al., 2016 Oncotarget 7: 18325-18345.*
Mavrommati et al., 2016 Sci Rep 6: 23277.*
Yoshioka et al., 2012, Nat Med 18: 1560-1569.*
Anquetil et al. EMBO Rep. Jun. 4, 2021; 22(6): e51299.*
Biswas et al: "Essential Role of Class II Phosphatidylinositol-3-kinase-C2α in Sphingosine 1-Phosphate Receptor-1-mediated Signaling and Migration in Endothelial Cells", The Journal of Biological Chemistry, vol. 288, No. 4, pp. 2325-2339, Jan. 25, 2013.
Oudit et al: "The role of phosphoinositide-3 kinase and PTEN in cardiovascular physiology and disease", Journal of Molecular and Cellular Cardiology, vol. 37, pp. 449-471, 2004.
Yoshioka et al: "PI3K-C2α, a class II PI3K, has an essential role in angiogenesis and vascular barrier function", Nature Medecine, vol. 18, No. 10, pp. 1560-1569, Oct. 2012.

* cited by examiner

SEQUENCE LISTING

```
<160> NUMBER OF SEQ ID NOS: 1

<210> SEQ ID NO 1
<211> LENGTH: 1634
<212> TYPE: PRT
<213> ORGANISM: Homo sapiens

<400> SEQUENCE: 1

Met Ser Ser Thr Gln Gly Asn Gly Glu His Trp Lys Ser Leu Glu Ser
1               5                   10                  15

Val Gly Ile Ser Arg Lys Glu Leu Ala Met Ala Glu Ala Leu Gln Met
            20                  25                  30
```

```
Glu Tyr Asp Ala Leu Ser Arg Leu Arg His Asp Lys Glu Glu Asn Arg
         35                  40                  45

Ala Lys Gln Asn Ala Asp Pro Ser Leu Ile Ser Trp Asp Glu Pro Gly
 50                  55                  60

Val Asp Phe Tyr Ser Lys Pro Ala Gly Arg Arg Thr Asp Leu Lys Leu
 65                  70                  75                  80

Leu Arg Gly Leu Ser Gly Ser Asp Pro Thr Leu Asn Tyr Asn Ser Leu
                 85                  90                  95

Ser Pro Gln Glu Gly Pro Pro Asn His Ser Thr Ser Gln Gly Pro Gln
            100                 105                 110

Pro Gly Ser Asp Pro Trp Pro Lys Gly Ser Leu Ser Gly Asp Tyr Leu
            115                 120                 125

Tyr Ile Phe Asp Gly Ser Asp Gly Gly Val Ser Ser Pro Gly Pro
        130                 135                 140

Gly Asp Ile Glu Gly Ser Cys Lys Lys Leu Ser Pro Pro Leu Pro
145                 150                 155                 160

Pro Arg Ala Ser Ile Trp Asp Thr Pro Pro Leu Pro Pro Arg Lys Gly
                165                 170                 175

Ser Pro Ser Ser Lys Ile Ser Gln Pro Ser Asp Ile Asn Thr Phe
            180                 185                 190

Ser Leu Val Glu Gln Leu Pro Gly Lys Leu Leu Glu His Arg Ile Leu
            195                 200                 205

Glu Glu Glu Glu Val Leu Gly Gly Gly Gln Gly Arg Leu Leu Gly
    210                 215                 220

Ser Val Asp Tyr Asp Gly Ile Asn Asp Ala Ile Thr Arg Leu Asn Leu
225                 230                 235                 240

Lys Ser Thr Tyr Asp Ala Glu Met Leu Arg Asp Ala Thr Arg Gly Trp
                245                 250                 255

Lys Glu Gly Arg Gly Pro Leu Asp Phe Ser Lys Asp Thr Ser Gly Lys
                260                 265                 270

Pro Val Ala Arg Ser Lys Thr Met Pro Pro Gln Val Pro Pro Arg Thr
            275                 280                 285

Tyr Ala Ser Arg Tyr Gly Asn Arg Lys Asn Ala Thr Pro Gly Lys Asn
            290                 295                 300

Arg Arg Ile Ser Ala Ala Pro Val Gly Ser Arg Pro His Thr Val Ala
305                 310                 315                 320

Asn Gly His Glu Leu Phe Glu Val Ser Glu Glu Arg Asp Glu Glu Val
                325                 330                 335

Ala Ala Phe Cys His Met Leu Asp Ile Leu Arg Ser Gly Ser Asp Ile
                340                 345                 350

Gln Asp Tyr Phe Leu Thr Gly Tyr Val Trp Ser Ala Val Thr Pro Ser
            355                 360                 365

Pro Glu His Leu Gly Asp Glu Val Asn Leu Lys Val Thr Val Leu Cys
    370                 375                 380

Asp Arg Leu Gln Glu Ala Leu Thr Phe Thr Cys Asn Cys Ser Ser Thr
385                 390                 395                 400

Val Asp Leu Leu Ile Tyr Gln Thr Leu Cys Tyr Thr His Asp Leu
            405                 410                 415

Arg Asn Val Asp Val Gly Asp Phe Val Leu Lys Pro Cys Gly Leu Glu
            420                 425                 430

Glu Phe Leu Gln Asn Lys His Ala Leu Gly Ser His Glu Tyr Ile Gln
            435                 440                 445
```

Tyr Cys Arg Lys Phe Asp Ile Asp Ile Arg Leu Gln Leu Met Glu Gln
450                 455                 460

Lys Val Arg Ser Asp Leu Ala Arg Thr Val Asn Asp Asp Gln Ser
465                 470                 475                 480

Pro Ser Thr Leu Asn Tyr Leu Val His Leu Gln Glu Arg Pro Val Lys
                    485                 490                 495

Gln Thr Ile Ser Arg Gln Ala Leu Ser Leu Leu Phe Asp Thr Tyr His
                500                 505                 510

Asn Glu Val Asp Ala Phe Leu Leu Ala Asp Gly Asp Phe Pro Leu Lys
                515                 520                 525

Ala Asp Arg Val Val Gln Ser Val Lys Ala Ile Cys Asn Ala Leu Ala
530                 535                 540

Ala Val Glu Thr Pro Glu Ile Thr Ser Ala Leu Asn Gln Leu Pro Pro
545                 550                 555                 560

Cys Pro Ser Arg Met Gln Pro Lys Ile Gln Lys Asp Pro Ser Val Leu
                565                 570                 575

Ala Val Arg Glu Asn Arg Glu Lys Val Val Glu Ala Leu Thr Ala Ala
                580                 585                 590

Ile Leu Asp Leu Val Glu Leu Tyr Cys Asn Thr Phe Asn Ala Asp Phe
            595                 600                 605

Gln Thr Ala Val Pro Gly Ser Arg Lys His Asp Leu Val Gln Glu Ala
        610                 615                 620

Cys His Phe Ala Arg Ser Leu Ala Phe Thr Val Tyr Ala Thr His Arg
625                 630                 635                 640

Ile Pro Ile Ile Trp Ala Thr Ser Tyr Glu Asp Phe Tyr Leu Ser Cys
                645                 650                 655

Ser Leu Ser His Gly Gly Lys Glu Leu Cys Ser Pro Leu Gln Thr Arg
                660                 665                 670

Arg Ala His Phe Ser Lys Tyr Leu Phe His Leu Ile Val Trp Asp Gln
                675                 680                 685

Gln Ile Cys Phe Pro Val Gln Val Asn Arg Leu Pro Arg Glu Thr Leu
        690                 695                 700

Leu Cys Ala Thr Leu Tyr Ala Leu Pro Ile Pro Pro Gly Ser Ser
705                 710                 715                 720

Ser Glu Ala Asn Lys Gln Arg Arg Val Pro Glu Ala Leu Gly Trp Val
                725                 730                 735

Thr Thr Pro Leu Phe Asn Phe Arg Gln Val Leu Thr Cys Gly Arg Lys
                740                 745                 750

Leu Leu Gly Leu Trp Pro Ala Thr Gln Glu Asn Pro Ser Ala Arg Trp
            755                 760                 765

Ser Ala Pro Asn Phe His Gln Pro Asp Ser Val Ile Leu Gln Ile Asp
        770                 775                 780

Phe Pro Thr Ser Ala Phe Asp Ile Lys Phe Thr Ser Pro Pro Gly Asp
785                 790                 795                 800

Lys Phe Ser Pro Arg Tyr Glu Phe Gly Ser Leu Arg Glu Glu Asp Gln
                805                 810                 815

Arg Lys Leu Lys Asp Ile Met Gln Lys Glu Ser Leu Tyr Trp Leu Thr
                820                 825                 830

Asp Ala Asp Lys Lys Arg Leu Trp Glu Lys Arg Tyr Tyr Cys His Ser
            835                 840                 845

Glu Val Ser Ser Leu Pro Leu Val Leu Ala Ser Ala Pro Ser Trp Glu
        850                 855                 860

-continued

```
Trp Ala Cys Leu Pro Asp Ile Tyr Val Leu Leu Lys Gln Trp Thr His
865                 870                 875                 880

Met Asn His Gln Asp Ala Leu Gly Leu Leu His Ala Thr Phe Pro Asp
                885                 890                 895

Gln Glu Val Arg Arg Met Ala Val Gln Trp Ile Gly Ser Leu Ser Asp
            900                 905                 910

Ala Glu Leu Leu Asp Tyr Leu Pro Gln Leu Val Gln Ala Leu Lys Tyr
        915                 920                 925

Glu Cys Tyr Leu Asp Ser Pro Leu Val Arg Phe Leu Leu Lys Arg Ala
    930                 935                 940

Val Ser Asp Leu Arg Val Thr His Tyr Phe Phe Trp Leu Leu Lys Asp
945                 950                 955                 960

Gly Leu Lys Asp Ser Gln Phe Ser Ile Arg Tyr Gln Tyr Leu Leu Ala
                965                 970                 975

Ala Leu Leu Cys Cys Cys Gly Lys Gly Leu Arg Glu Glu Phe Asn Arg
            980                 985                 990

Gln Cys Trp Leu Val Asn Ala Leu Ala Lys Leu Ala Gln Gln Val Arg
        995                 1000                1005

Glu Ala Ala Pro Ser Ala Arg Gln Gly Ile Leu Arg Thr Gly Leu
    1010                1015                1020

Glu Glu Val Lys Gln Phe Phe Ala Leu Asn Gly Ser Cys Arg Leu
    1025                1030                1035

Pro Leu Ser Pro Ser Leu Leu Val Lys Gly Ile Val Pro Arg Asp
    1040                1045                1050

Cys Ser Tyr Phe Asn Ser Asn Ala Val Pro Leu Lys Leu Ser Phe
    1055                1060                1065

Gln Asn Val Asp Pro Leu Gly Glu Asn Ile Arg Val Ile Phe Lys
    1070                1075                1080

Cys Gly Asp Asp Leu Arg Gln Asp Met Leu Thr Leu Gln Met Ile
    1085                1090                1095

Arg Ile Met Ser Lys Ile Trp Val Gln Glu Gly Leu Asp Met Arg
    1100                1105                1110

Met Val Ile Phe Arg Cys Phe Ser Thr Gly Arg Gly Arg Gly Met
    1115                1120                1125

Val Glu Met Ile Pro Asn Ala Glu Thr Leu Arg Lys Ile Gln Val
    1130                1135                1140

Glu His Gly Val Thr Gly Ser Phe Lys Asp Arg Pro Leu Ala Asp
    1145                1150                1155

Trp Leu Gln Lys His Asn Pro Gly Glu Asp Glu Tyr Glu Lys Ala
    1160                1165                1170

Val Glu Asn Phe Ile Tyr Ser Cys Ala Gly Cys Cys Val Ala Thr
    1175                1180                1185

Tyr Val Leu Gly Ile Cys Asp Arg His Asn Asp Asn Ile Met Leu
    1190                1195                1200

Lys Thr Thr Gly His Met Phe His Ile Asp Phe Gly Arg Phe Leu
    1205                1210                1215

Gly His Ala Gln Met Phe Gly Asn Ile Lys Arg Asp Arg Ala Pro
    1220                1225                1230

Phe Val Phe Thr Ser Asp Met Ala Tyr Val Ile Asn Gly Gly Asp
    1235                1240                1245

Lys Pro Ser Ser Arg Phe His Asp Phe Val Asp Leu Cys Cys Gln
    1250                1255                1260
```

```
Ala Tyr Asn Leu Ile Arg Lys His Thr His Leu Phe Leu Asn Leu
1265                1270                1275

Leu Gly Leu Met Leu Ser Cys Gly Ile Pro Glu Leu Ser Asp Leu
1280                1285                1290

Glu Asp Leu Lys Tyr Val Tyr Asp Ala Leu Arg Pro Gln Asp Thr
1295                1300                1305

Glu Ala Asn Ala Thr Thr Tyr Phe Thr Arg Leu Ile Glu Ser Ser
1310                1315                1320

Leu Gly Ser Val Ala Thr Lys Leu Asn Phe Phe Ile His Asn Leu
1325                1330                1335

Ala Gln Met Lys Phe Thr Gly Ser Asp Asp Arg Leu Thr Leu Ser
1340                1345                1350

Phe Ala Ser Arg Thr His Thr Leu Lys Ser Ser Gly Arg Ile Ser
1355                1360                1365

Asp Val Phe Leu Cys Arg His Glu Lys Ile Phe His Pro Asn Lys
1370                1375                1380

Gly Tyr Ile Tyr Val Val Lys Val Met Arg Glu Asn Thr His Glu
1385                1390                1395

Ala Thr Tyr Ile Gln Arg Thr Phe Glu Glu Phe Gln Glu Leu His
1400                1405                1410

Asn Lys Leu Arg Leu Leu Phe Pro Ser Ser His Leu Pro Ser Phe
1415                1420                1425

Pro Ser Arg Phe Val Ile Gly Arg Ser Arg Gly Glu Ala Val Ala
1430                1435                1440

Glu Arg Arg Arg Glu Glu Leu Asn Gly Tyr Ile Trp His Leu Ile
1445                1450                1455

His Ala Pro Pro Glu Val Ala Glu Cys Asp Leu Val Tyr Thr Phe
1460                1465                1470

Phe His Pro Leu Pro Arg Asp Glu Lys Ala Met Gly Thr Ser Pro
1475                1480                1485

Ala Pro Lys Ser Ser Asp Gly Thr Trp Ala Arg Pro Val Gly Lys
1490                1495                1500

Val Gly Gly Glu Val Lys Leu Ser Ile Ser Tyr Lys Asn Asn Lys
1505                1510                1515

Leu Phe Ile Met Val Met His Ile Arg Gly Leu Gln Leu Leu Gln
1520                1525                1530

Asp Gly Asn Asp Pro Asp Pro Tyr Val Lys Ile Tyr Leu Leu Pro
1535                1540                1545

Asp Pro Gln Lys Thr Thr Lys Arg Lys Thr Lys Val Ala Arg Lys
1550                1555                1560

Thr Cys Asn Pro Thr Tyr Asn Glu Met Leu Val Tyr Asp Gly Ile
1565                1570                1575

Pro Lys Gly Asp Leu Gln Gln Arg Glu Leu Gln Leu Ser Val Leu
1580                1585                1590

Ser Glu Gln Gly Phe Trp Glu Asn Val Leu Leu Gly Glu Val Asn
1595                1600                1605

Ile Arg Leu Arg Glu Leu Asp Leu Ala Gln Glu Lys Thr Gly Trp
1610                1615                1620

Phe Ala Leu Gly Ser Arg Ser His Gly Thr Leu
1625                1630
```

USE OF PI3KC2B INHIBITORS FOR THE PRESERVATION OF VASCULAR ENDOTHELIAL CELL BARRIER INTEGRITY

FIELD OF THE INVENTION

The present invention relates to the use of PI3KC2β inhibitors for the preservation of vascular endothelial cell barrier integrity.

BACKGROUND OF THE INVENTION

Ischemic conditions are a leading cause of death for both men and women. Ischemia, a condition characterized by reduced blood flow and oxygen to an organ. For instance ischemic injuries may occur in various organs and tissues, including the heart, which can lead to myocardial infarction and the brain, which can lead to stroke ischemia. Re-establishment of blood flow, or reperfusion, and re-oxygenation of the affected area following an ischemic episode is critical to limit irreversible damage. However, reperfusion also associates potentially damaging consequences. For instance, increased vascular permeability is an important contributor to edema and tissue damage following ischemic events. Development of edema determines disruption of integrity which is detrimental to recovery and also permits extravasation of fibronectin and fibrinogen that form the provisional matrix network used by leukocytes for infiltrating. Vascular damage also contributes to the no-reflow phenomenon which is observed in 30% of patients with a reperfused anterior wall myocardial ischemia and is associated with a higher incidence of death. Leakiness of blood vessels in the tissues therefore contributes to disease progression. The prevalence of ischemic conditions necessitates the development of therapies and therapeutic agents that can effectively prevent, reduce, or counteract ischemia and ischemia-reperfusion injury. Thus, there is a significant need for new and more effective therapies and therapeutic agents for the treatment of ischemia and ischemia-reperfusion injuries.

SUMMARY OF THE INVENTION

The present invention relates to the use of PI3KC2β inhibitors for the preservation of vascular endothelial cell barrier integrity. In particular, the present invention is defined by the claims.

DETAILED DESCRIPTION OF THE INVENTION

The first object of the present invention relates to a method for the preservation of vascular endothelial cell barrier integrity in a patient in need thereof comprising administering to the subject a therapeutically effective amount of a PI3KC2β inhibitor.

As used herein, the term "vascular endothelial cell barrier" refers to the layer of cells that line the interior surface of blood vessels and act as a selective barrier between the vessel lumen and surrounding tissue, by controlling the transit of fluids, materials and cells such as myeloid cells and white blood cells into and out of the bloodstream. Excessive or prolonged increases in permeability of vascular endothelial cell barrier leads to tissue oedema/swelling. Accordingly the term "preservation of vascular endothelial cell barrier integrity" means the maintenance of the vascular endothelial cell barrier by avoiding or limiting permeability of said barrier.

In some embodiments, the PI3KC2β inhibitor of the present invention is particularly suitable for the preservation of vascular endothelial cell barrier integrity during sepsis. As used herein, the term "sepsis" has its general meaning in the art and represents a serious medical condition that is characterized by a whole-body inflammatory state. In addition to symptoms related to the provoking infection, sepsis is characterized by presence of acute inflammation present throughout the entire body, and is, therefore, frequently associated with fever and elevated white blood cell count (leukocytosis) or low white blood cell count and lower-than-average temperature, and vomiting. In particular, sepsis is defined as a deregulated immune response to infection, translating into life-threatening organs dysfunction, defined by a Sequential Organ Failure Assessment score of 2 more. Infection can be suspected or proven, or a clinical syndrome pathognomonic for infection. Septic shock is defined by infection and the need for vasopressors to maintain mean blood pressure ≥65 mmHg and arterial lactate levels >2 mmol/l.

In some embodiments, the PI3KC2β inhibitor of the present invention is particularly suitable for the preservation of vascular endothelial cell barrier integrity during the treatment of ischemic conditions.

As used herein, the term "ischemic condition" has its general meaning in the art and refers to any condition that result from ischemia. As used herein, the term "ischemia" as used herein refers to a restriction in blood supply with resultant damage or dysfunction of the organ. Rather than hypoxia (a more general term denoting a shortage of oxygen, usually a result of lack of oxygen in the air being breathed), ischemia is an absolute or relative shortage of the blood supply to an organ, i.e. a shortage of oxygen, glucose and other blood-borne components. For example ischemic conditions include but are not limited to renal ischemia, retinal ischemia, brain ischemia and myocardial ischemia. More particularly, the term includes but it is not limited to coronary artery bypass graft surgery, global cerebral ischemia due to cardiac arrest, focal cerebral infarction, carotid stenosis or occlusion leading to cerebral ischemia, cardiogenic thromboembolism, stroke, spinal stroke and spinal cord injury.

In some embodiments, the method of the present invention is particularly suitable for the treatment of an acute ischemic stroke. As used herein, the term "acute ischemic stroke" or 'AIS" refers to those patients having or at risk for "definite acute ischemic cerebrovascular syndrome (AICS)" as defined by the diagnostic criteria of Kidwell et al. "Acute Ischemic Cerebrovascular Syndrome: Diagnostic Criteria," Stroke, 2003, 34, pp. 2995-2998 (incorporated herein by reference). Accordingly, acute ischemic stroke refers to an acute onset of neurologic dysfunction of any severity consistent with focal brain ischemia.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the PI3KC2β inhibitor of the present invention is particularly suitable for reducing infarct size, preventing or reducing edema, preventing hemorrhage and preventing no-reflow. As used herein, the term "no-reflow" has been increasingly used in published medical reports to describe microvascular obstruction and reduced flow after opening an occluded artery. In its broadest meaning, the term "preventing no-reflow" or "prevention of no-reflow" refers to reducing or avoiding the no-reflow.

In some embodiments, the PI3KC2β inhibitor of the present invention is particularly suitable for preventing ischemia-reperfusion injuries. As used herein, the term "reperfusion" has its general meaning in the art and refers to the restoration of blood flow to a tissue following ischemia. Accordingly, the term "ischemia reperfusion" is thus intended to encompass an event wherein an episode of ischemia is followed by an episode of reperfusion and the term "ischemia reperfusion injury" refers to the tissue damage caused by an ischemia reperfusion event.

In some embodiments, the method of the present invention is performed sequentially or concomitantly with a standard method for treating ischemic conditions. Typically, standard methods include reperfusion of the ischemic organ by angioplasty, thrombolysis, or surgical thrombectomy. The term "thrombolysis" means the administration of thrombolytic agents. Typically thrombolysis involves the use of t-PA. As used herein, the term "t-PA" has its general meaning in the art and refers to tissue-type plasminogen activator. The term includes native t-PA and recombinant t-PA, as well as modified forms of t-PA that retain the enzymatic or fibrinolytic activities of native t-PA. The enzymatic activity of t-PA can be measured by assessing the ability of the molecule to convert plasminogen to plasmin. The fibrinolytic activity of t-PA may be determined by any in vitro clot lysis activity known in the art. Recombinant t-PA has been described extensively in the prior art and is known to the person of skill. t-PA is commercially available as alteplase (Activase® or Actilyse®). Modified forms of t-PA ("modified t-PA") have been characterized and are known to those skilled in the art. Modified t-PAs include, but are not limited to, variants having deleted or substituted amino acids or domains, variants conjugated to or fused with other molecules, and variants having chemical modifications, such as modified glycosylation. Several modified t-PAs have been described in PCT Publication No. WO93/24635; EP352,119; EP382174. In some embodiments, the modified form of t-PA is Tenecteplase. As used herein, the term "tenecteplase," also known as TNK-t-PA or TNKASE™ brand of tissue-plasminogen activator variant, refers to a t-PA variant designated T103N, N117Q, K296A, H297A, R298A, R299A t-PA available from Genentech, Inc. (South San Francisco Calif.) wherein Thr103 of wild-type t-PA is changed to Asn (T103N), Asn 117 of wild-type t-PA is changed to Gln (N117Q), and Lys-His-Arg-Arg 296-299 of wild-type t-PA is changed to Ala-Ala-Ala-Ala (KHRR296-299AAAA). Tenecteplase is a genetically engineered variant of human t-PA cloned and expressed in Chinese hamster ovary cells (see Keyt et al., Proc. Natl. Acad. Sci USA, 91: 3670-3674 (1994) and Verstraete, Am. J. Med, 109: 52-58 (2000) for an overview of third-generation thrombolytic drugs in general). Tenecteplase was engineered to have increased fibrin specificity and an increased half-life compared to alteplase.

In some embodiments, the present invention relates to method of treating an ischemic condition in a patient in need thereof comprising the steps consisting of i) restoring blood supply in the ischemic tissue, and preserving the vascular endothelial cell barrier integrity of said ischemic tissue by administering to said patient a therapeutically effective amount of PI3KC2β inhibitor.

As used herein, the term "PI3KC2β" has its general meaning in the art and refers to the phosphatidylinositol 4-phosphate 3-kinase C2 domain-containing subunit beta, encoded by the PIK3C2B gene (Gene ID: 5287). The protein belongs to the phosphoinositide 3-kinase (PI3K) family and contains a lipid kinase catalytic domain as well as a C-terminal C2 domain, a characteristic of class II PI3-kinases. C2 domains act as calcium-dependent phospholipid binding motifs that mediate translocation of proteins to membranes, and may also mediate protein-protein interactions. The term is also known as C2-PI3K or phosphoinositide 3-kinase-C2-beta. An exemplary human amino acid sequence is represented by SEQ ID NO:1.

SEQ ID NO:1>sp1000750IP3C2B_HUMAN Phosphatidylinositol 4-phosphate 3-kinase C2 domain-containing subunit beta OS=Homo sapiens OX=9606 GN=PIK3C2B PE=1 SV=2 MSSTQGNGEHWKSLESVGISRKE-LAMAEALQMEYDALSRLRHDKEEN-RAKQNADPSLISW DEPGVDFYSKPAGRRTDLKLLR-GLSGSDPTLNYNSLSPQEGPPNHST-SQGPQPGSDPWPK GSLSGDY-LYIFDGSDGGVSSSPGPGDIEGSCKKLSPPPLPPR-ASIWDTPPLPPRKGSPSS SKISQPSDINTFSLVEQLPGKLLEHRI-LEEEEVLGGGGQGRLLGSVDYDGINDAITRLNL KSTYDAEMLRDATRGWKEGRG-PLDFSKDTSGKPVARSKTMPPQVPPRTYASRYG-NRKNAT PGKNRRISAAPVGSRPHTVANGHELF-EVSEERDEEVAAFCHMLDILRSGSDIQDYFLTGY VWSAVTPSPEHLGDEVNLKVTVLCDRLQEALT-FTCNCSSTVDLLIYQTLCYTHDDLRNVD VGDFVLKPCGLEEFLQNKHALGSHEYIQYCRKF-DIDIRLQLMEQKVVRSDLARTVNDDQS PSTL-NYLVHLQERPVKQTISRQALSLLFDTYH- NEVDAFLLADGDFPLKADRVVQSVKAIC NAL-
AAVETPEITSALNQLPPCPSRMQPKIQKDPSV-
LAVRENREKVVEALTAAILDLVELY
CNTFNADFQTAVPGSRKHDLVQEACH-
FARSLAFTVYATHRIPIIWATSYEDFYLSCSLSH
GGKELCSPLQTRRAHFSKY-
LFHLIVWDQQICFPVQVNRLPRETLLCATLYAL-
PIPPPGSS SEANKQRRVPEALGWVTTPLFN-
FRQVLTCGRKLLGLWPATQENPSARWSAPNFH-
QPDSVI LQIDFPT-
SAFDIKFTSPPGDKFSPRYEFGSL-
REEDQRKLKDIMQKESLYWLTDADKKRLW
EKRYYCHSEVSSLPLVLASAPSWEWA-
CLPDIYVLLKQWTHMNHQDALGLL-
HATFPDQEVR RMAVQWIGSLSDAELL-
DYLPQLVQALKYECYLDSPLVRFLLKRAVSDLR-
VTHYFFWLLKD GLKDSQFSIRYQYL-
LAALLCCCGKGLREEFNRQCWLVNALAK-
LAQQVREAAPSARQGILR TGLEEVKQFFALNG-
SCRLPLSPSLLVKGIVPRDCSYFNSNAVPLKLSF-
QNVDPLGENIRV IFKCGDDLRQDMLTLQMIRIM-
SKIWVQEGLDMRMVIFRCFSTGRGRGMVEMIP-
NAETLRK IQVEHGVTGSFKDR-
PLADWLQKHNPGEDEYEKAVENFIYSCAGCC-
VATYVLGICDRHNDN
IMLKTTGHMFHIDFGRFLGHAQMFGNIKRDRA-
PFVFTSDMAYVINGGDKPSSRFHDFVDL
CCQAYNLIRKHTHLFLNLLGLMLSCGIPELS-
DLEDLKYVYDALRPQDTEANATTYFTRLI
ESSLGSVATKLNFFIHNLAQMKFTGSDDRLTLS-
FASRTHTLKSSGRISDVFLCRHEKIFH
PNKGYIYVVKVMRENTHEATYIQRT-
FEEFQELHNKLRLLFPSSHLPSFPSRFVIGRSRGE
AVAERRREELNGYIWHLIHAPPE-
VAECDLVYTFFHPLPRDEKAMGTSPAPKSSDGT-
WARP VGKVGGEVKLSISYKNNKLFIMVMHIR-
GLQLLQDGNDPDPYVKIYLLPDPQKTTKRKTKV
ARKTCNPTYNEMLVYDG-
IPKGDLQQRELQLSVLSEQGFWENVLL-
GEVNIRLRELDLAQEK TGWFALGSRSHGTL As used herein, a "PI3KC2β inhibitor" refers to any compound natural or not which is capable of inhibiting the activity of PI3KC2β, in particular PI3KC2β kinase activity. The term encompasses any PI3KC2B inhibitor that is currently known in the art or that will be identified in the future, and includes any chemical entity that, upon administration to a patient, results in inhibition or down-regulation of a biological activity associated with activation of the PI3KC2β. The term also encompasses inhibitor of expression. In some embodiments, the PI3KC2β inhibitor is selective over the other kinases. By "selective" it is meant that the inhibition of the selected compound is at least 10-fold, preferably 25-fold, more preferably 100-fold, and still preferably 300-fold higher than the inhibition of the other PI3K kinases. The PI3KC2β inhibition of the compounds may be determined using various methods well known in the art.

In some embodiments, the PI3KC2β inhibitor is a small organic molecule.

In some embodiments, the PI3KC2β inhibitor is an inhibitor of PI3KC2β expression. An "inhibitor of expression" refers to a natural or synthetic compound that has a biological effect to inhibit the expression of a gene. In some embodiments, said inhibitor of gene expression is a siRNA, an antisense oligonucleotide or a ribozyme. For example, anti-sense oligonucleotides, including anti-sense RNA molecules and anti-sense DNA molecules, would act to directly block the translation of PI3KC2β mRNA by binding thereto and thus preventing protein translation or increasing mRNA degradation, thus decreasing the level of PI3KC2β, and thus activity, in a cell. For example, antisense oligonucleotides of at least about 15 bases and complementary to unique regions of the mRNA transcript sequence encoding PI3KC2β can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. PI3KC2β gene expression can be reduced by contacting a subject or cell with a small double stranded RNA (dsRNA), or a vector or construct causing the production of a small double stranded RNA, such that PI3KC2β gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing PI3KC2β. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

According to the invention, the PI3KC2β inhibitor is administered to the patient in a therapeutically effective amount. By a "therapeutically effective amount" is meant a sufficient amount of the active ingredient for treating or reducing the symptoms at reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination with the active ingredients; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically the active ingredient of the present invention (e.g. PI3KC2β inhibitor) is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

A further aspect of the invention relates to a method for screening a plurality of test substances useful for the treatment of an ischemic condition in a patient in need thereof comprising the steps consisting of (a) testing each of the test substances for its ability to inhibit the activity or expression of PI3KC2β and (b) and positively selecting the test substances capable of said inhibition.

In some embodiments, the screening method of the present invention comprises the step of (i) providing a PI3KC2β protein; (ii) contacting the PI3KC2β protein with a test substance wherein the substance is expected to inhibit the kinase activity of the PI3KC2β protein; and (iii) selecting a test substance as a candidate that decreases the kinase activity of PI3KC2β in comparison to a negative control that is not contacted with a test substance.

Typically, PI3KC2β protein come from various sources and sequences in the art may be used for the present disclosure as long as it contains a kinases activity. In one embodiment, a full or partial length of PI3KC2β can be used (e.g. SEQ ID NO:1).

In some embodiments, PI3KC2β protein is provided as a cell that endogenously or exogenously express the protein. For example, mammalian cells are prepared to express the protein of interest such as PI3KC2β through a transient or stable transfection or cells that endogenously express the protein of interest may be used. Cells endogenously expressing PI3KC2β may include but is not limited to endothelial cells. The cells obtained may be cultured in a cell culture dish and treated with a test substance for a certain period time in a suitable medium, from which the whole proteins are extracted and tested/detected for kinase activity of PI3KC2β protein. Alternatively established cell lines may be used, in which case the cells are transfected with a plasmid expressing PI3KC2β. The example of such cells include but is not limited to 293, 293T or 293A (Graham F L, Smiley J, Russell W C, Nairn R (July 1977). "Characteristics of a human cell line transformed by DNA from human adenovirus type 5". J. Gen. Virol. 36 (1): 59-74; and Louis N, Evelegh C, Graham F L (July 1997). "Cloning and sequencing of the cellular-viral junctions from the human adenovirus type 5 transformed 293 cell line". Virology 233 (2): 423-9).

The term "test substance" refers generally to a material that is expected to decrease, reduce, suppress or inhibit the kinase activity of PI3KC2β, which include small molecules, high molecular weight molecules, mixture of compounds such as natural extracts or cell or tissue culture products, biological material such as proteins, antibodies, peptides, DNA, RNA, antisense oligonucleotides, RNAi, aptamer, RNAzymes and DNAzymes, or glucose and lipids, but is not limited thereto. The test substances may be polypeptides having amino acid residues of below 20, particularly 6, 10, 12, 20 aa or above 20 such as 50aa. These materials are obtained from synthetic or natural compound libraries and the methods to obtain or construct libraries are known in the art. For example, synthetic chemical library may be obtained from Maybridge Chemical Co. (UK), Comgenex(USA), Brandon Associates(USA), Microsource(USA) and Sigma-Aldrich(USA). The chemical library of natural origin may be obtained from Pan Laboratories (USA) and MycoSearch (USA). Further test substances may be obtained by various combinatorial library construction methods known in the art including for example, biological libraries, spatially addressable parallel solid phase or solution phase libraries. Test substance of a library may be composed of peptides, peptoids, circular or liner oligomeric compounds, template based compounds such as benzodiazepine, hydantoin, biaryls, carbocyclic and polycyclic compounds such as naphthalene, phenothiazine, acridine, steroids and the like, carbohydrate and amino acid derivatives, dihydropyridine, benzhydryl and heterocyclic compounds such as triazine, indole, thiazolidine and the like, but does not limited thereto.

The invention will be further illustrated by the following figures and examples. However, these examples and figures should not be interpreted in any way as limiting the scope of the present invention.

FIGURES

Figure 1C:
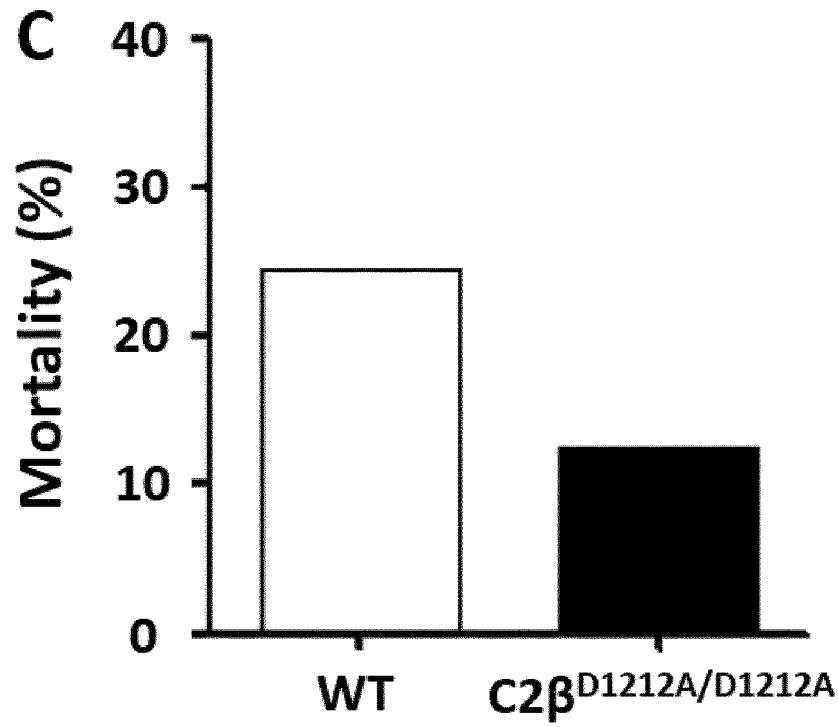
Figure 1D:
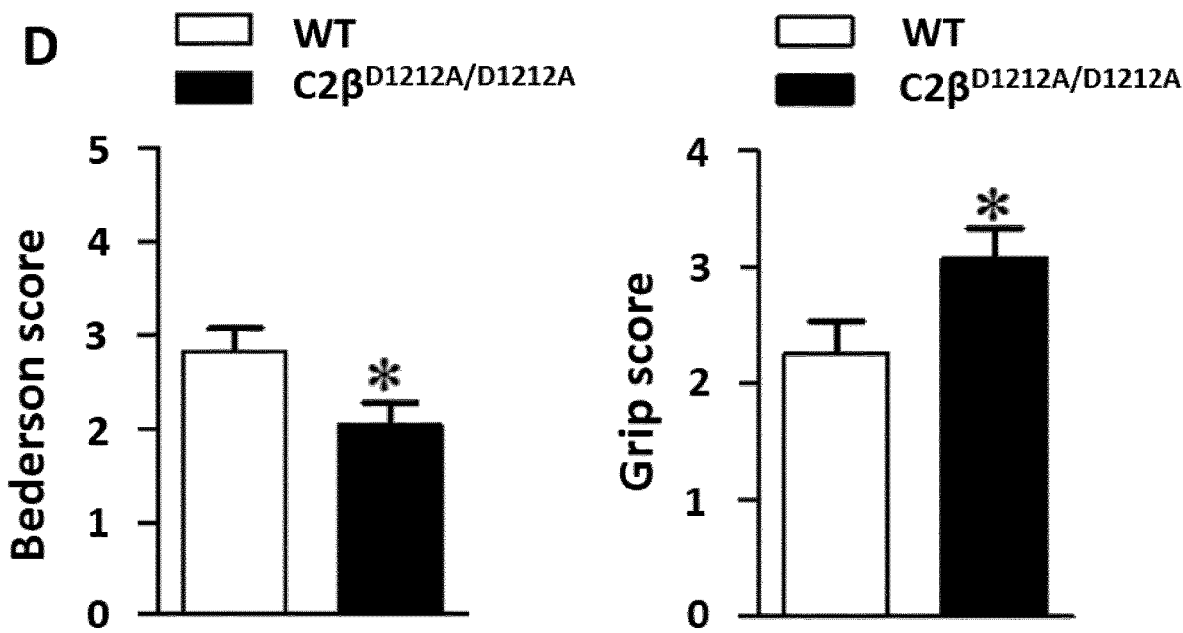

FIG. 1 Genetic inhibition of PI3K-C2β reduces cerebral infarction in two ischemia/reperfusion (I/R) models and improves neurological outcome. (A) Graph quantification of infarct volume measurements at 24 hours after thromboembolic stroke in wild-type (WT) and $C2\beta^{D1212A/D1212A}$ mice showing a smaller ischemic lesion in the $C2\beta^{D1212A/D1212A}$ animals (PI3KC2β KI mice) (n=17-19 mice per group; *P<0.001, unpaired t-test). (B) Graph quantification of infarct volume measurements in wild-type (WT), heterozygous (C2β$^{WT/D1212A}$) and homozygous (C2β$^{D1212A/D1212A}$) mice subjected to transient middle cerebral artery occlusion (tMCAO) for 1 h followed by 24 h reperfusion (n=14-27 mice per group). P<0.01; ***P<0.001, unpaired t-test. SHAM: operated WT mice without monofilament insertion. Results show a smaller ischemic lesion according to the level of PI3KC2β inhibition. (C) Mortality evaluation of 10-week-old C2β$^{D1212A/D1212A}$ and WT mice between day 0 and day 1 after tMCAO showing a better survival when PI3KC2β is inactive (n=30-39 per group). (D) Neurological scores evaluated at 24 h by Bederson (left panel) and Grip (right panel) test based on a five point system (n=27 mice per group; *P<0.05, Mann-Whitney test).

Figures 2A, 2B:
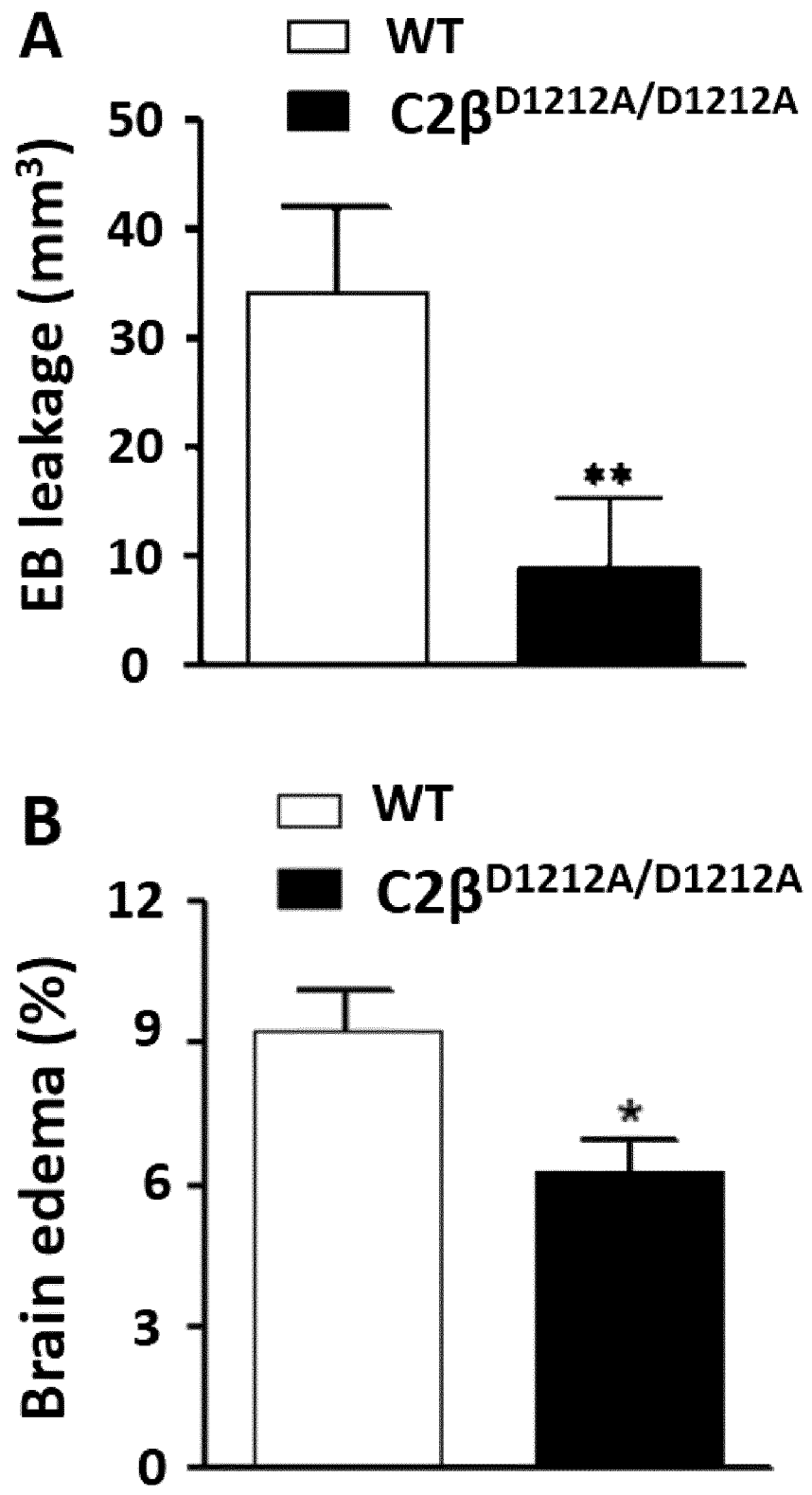
Figure 2:
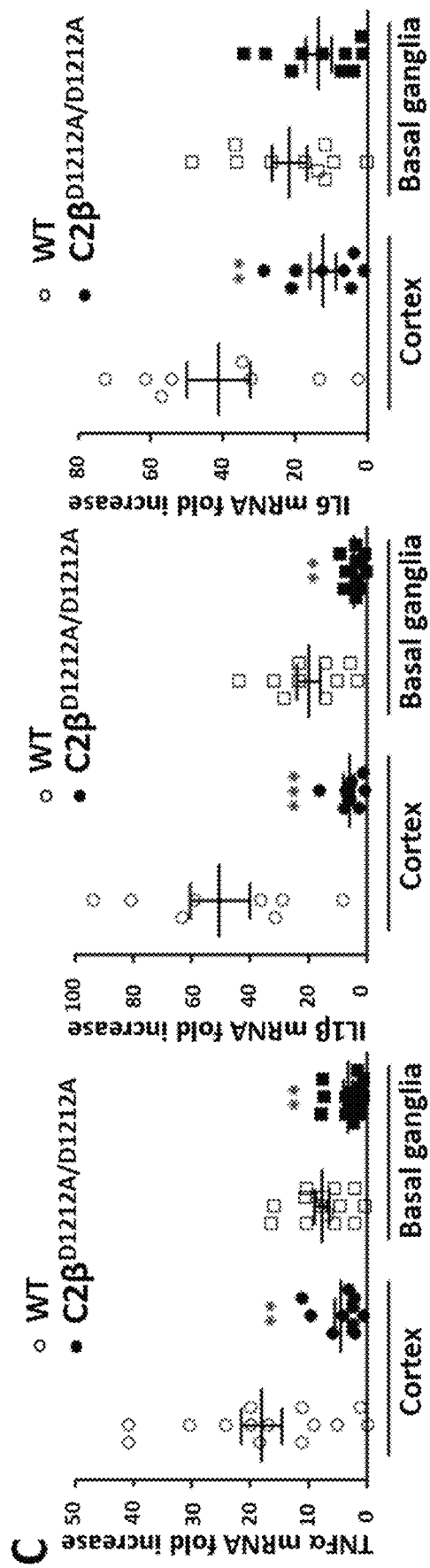
Figure 2D:
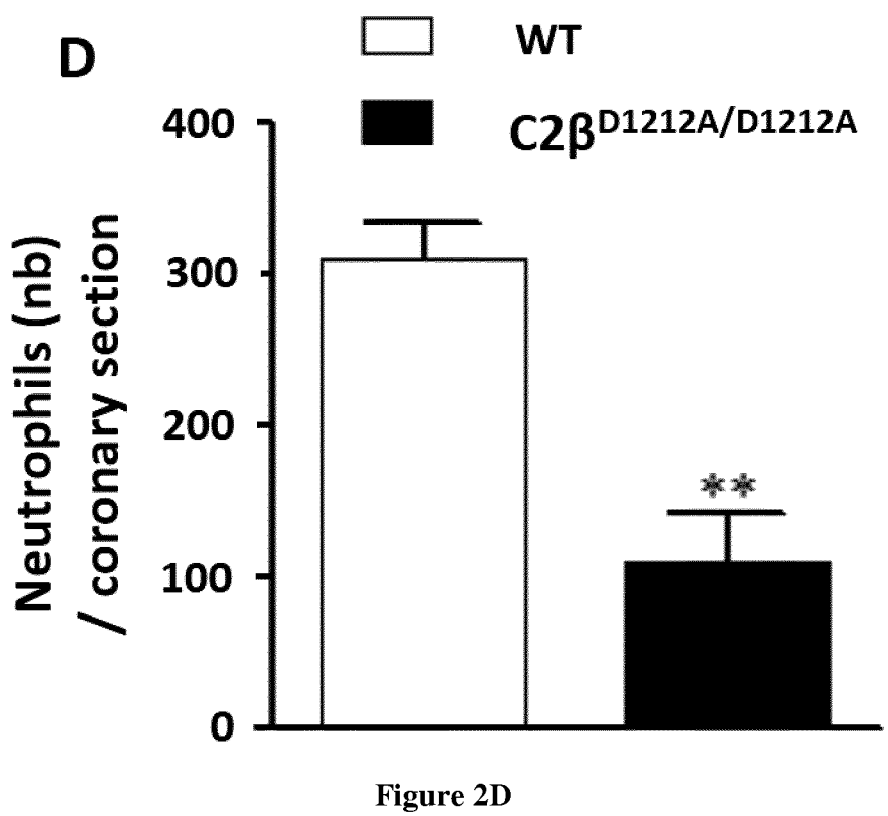
Figure 2E:
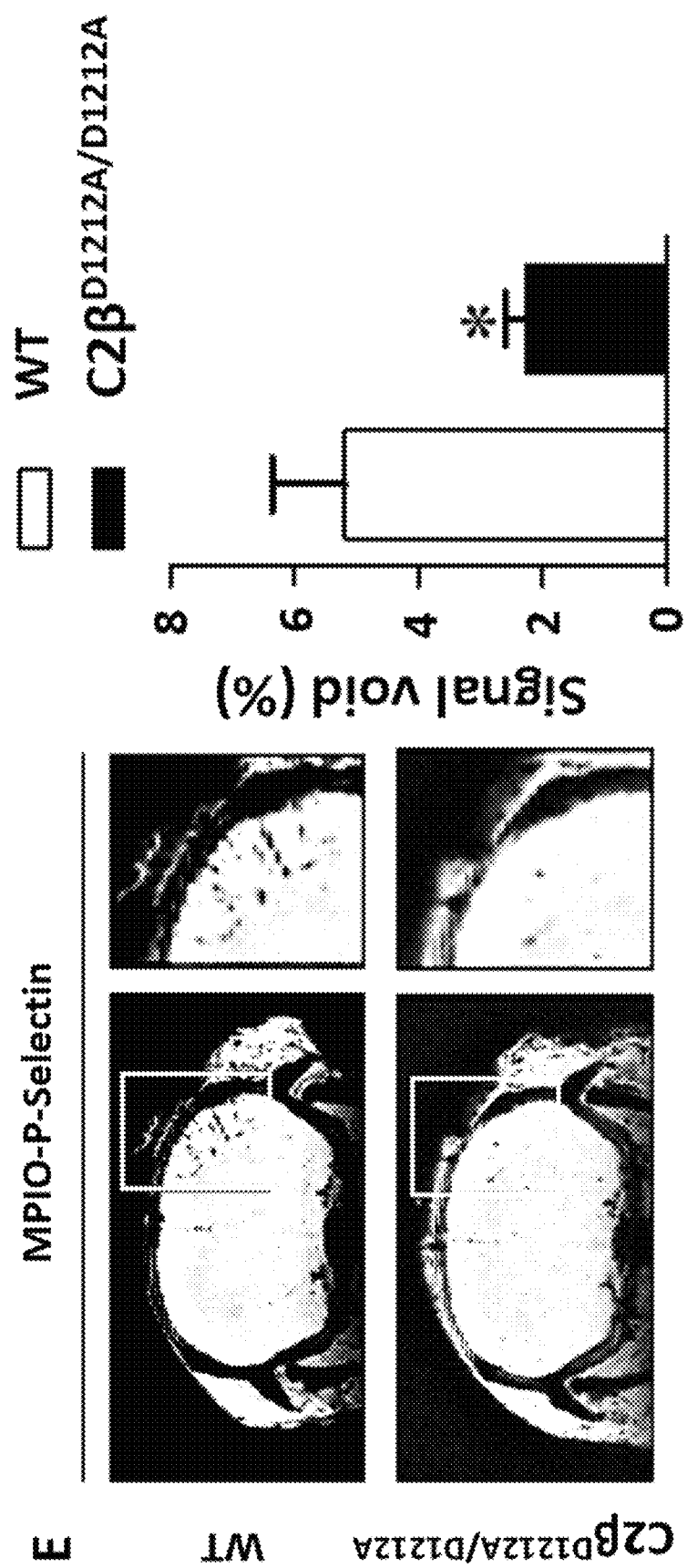

FIG. 2 Genetic inhibition of PI3K-C2β stabilizes the blood-brain barrier (BBB) after ischemic stroke and reduces inflammation. Leakage of Evans blue dye in brain parenchyma (A-B) Graph quantification of Evans blue dye extravasation measurements in wild-type (WT) and PI3KC2β KI (C2β$^{D1212A/D1212A}$) mice subjected to transient middle cerebral artery occlusion (tMCAO) for 1 h followed by 24 h reperfusion (n=10-16 mice per group). P<0.01; Mann Whitney test. (C) Genetic inhibition of PI3K-C2β reduces inflammation—Relative gene expression of interleukin-1β (IL-1β), interleukin-6 (IL-6) and tumor necrosis factor (TNFα) 24 hours following tMCAO in the cortex and basal ganglia of control (WT) and PI3KC2β KI (C2β$^{D1212A/D1212A}$) mice. The mRNA levels are given as the fold increase normalized to rps29 relative to the corresponding contralateral hemisphere; TNFα (n=10-14 mice per group); IL-1p, IL-6 (n=8-10 mice per group). Data represent mean±SEM, P<0.01; *P=0.001; Unpaired t-test with Welch's correction. (D) Genetic inhibition of PI3K-C2β reduces neutrophils recruitment—Graph quantification for neutrophils infiltration in the ischemic hemisphere of wild-type (WT) and PI3KC2β KI (C2β$^{D1212A/D1212A}$) mice subjected to tMCAO for 1 h followed by 24 h reperfusion (n=6 mice per group). P<0.01; Mann Whitney test. (E) Representative T2-weighted MRI of WT and C2β$^{D1212A/D1212A}$ mice taken 24 hours after the onset of in situ clot formation by alpha thrombin, and graph quantification of area stained by P-Selectin using MPIOs in ipsilateral normalize to contralateral cortex in percentage (n=10-11 mice per group; *P<0.05; Unpaired t-test with Welch's correction).

Figure 3A:
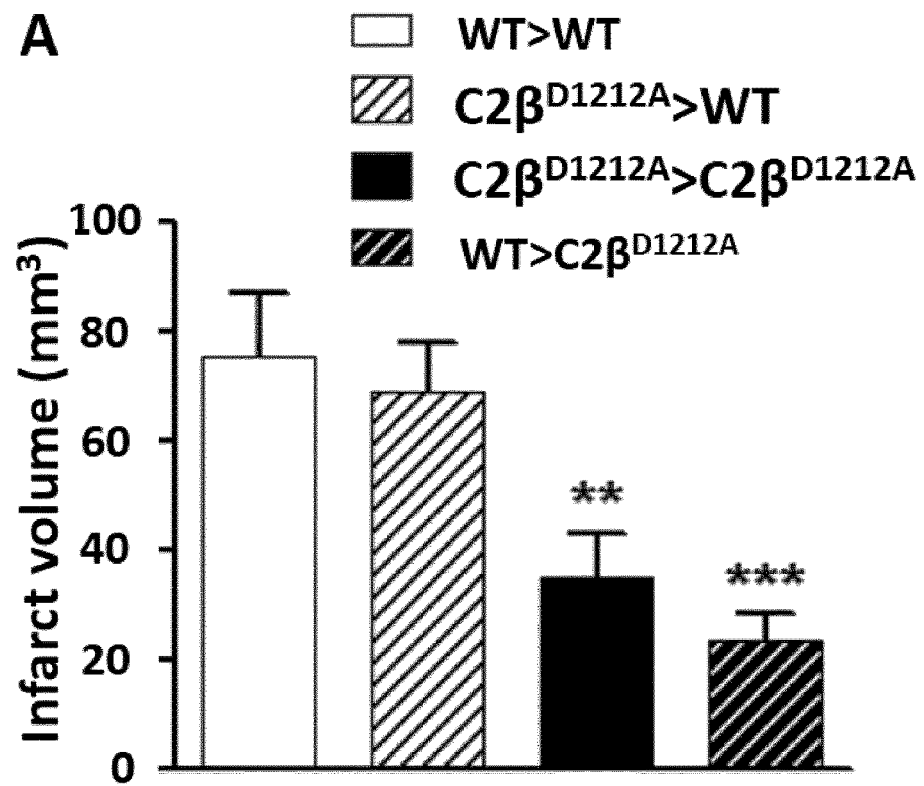
Figure 3B:
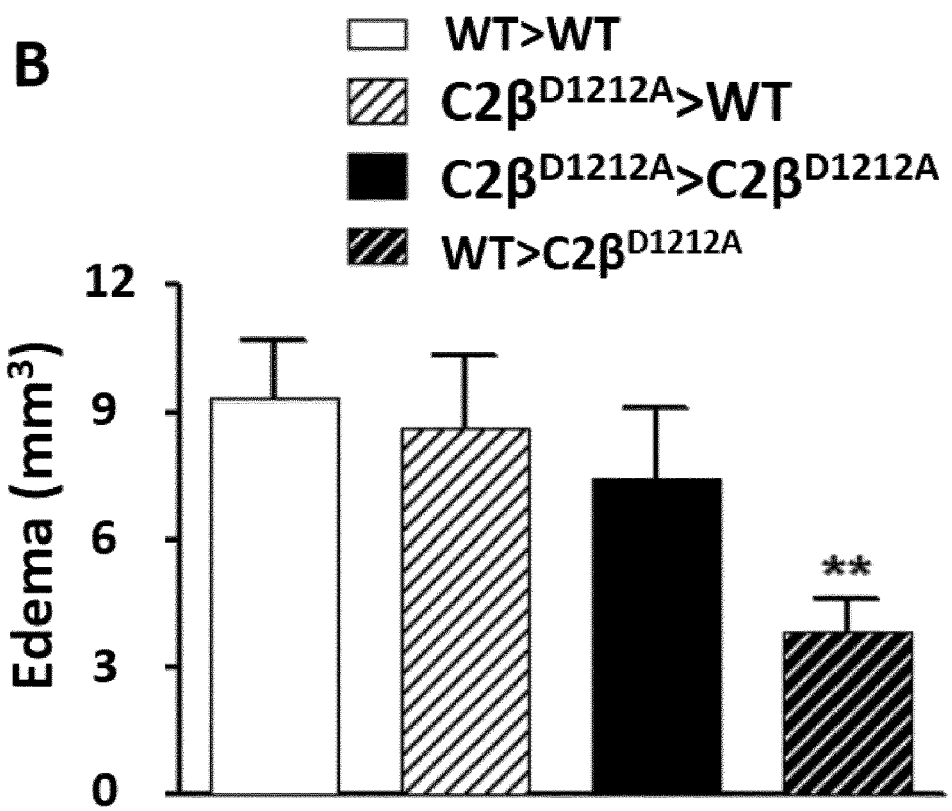
Figure 3C:
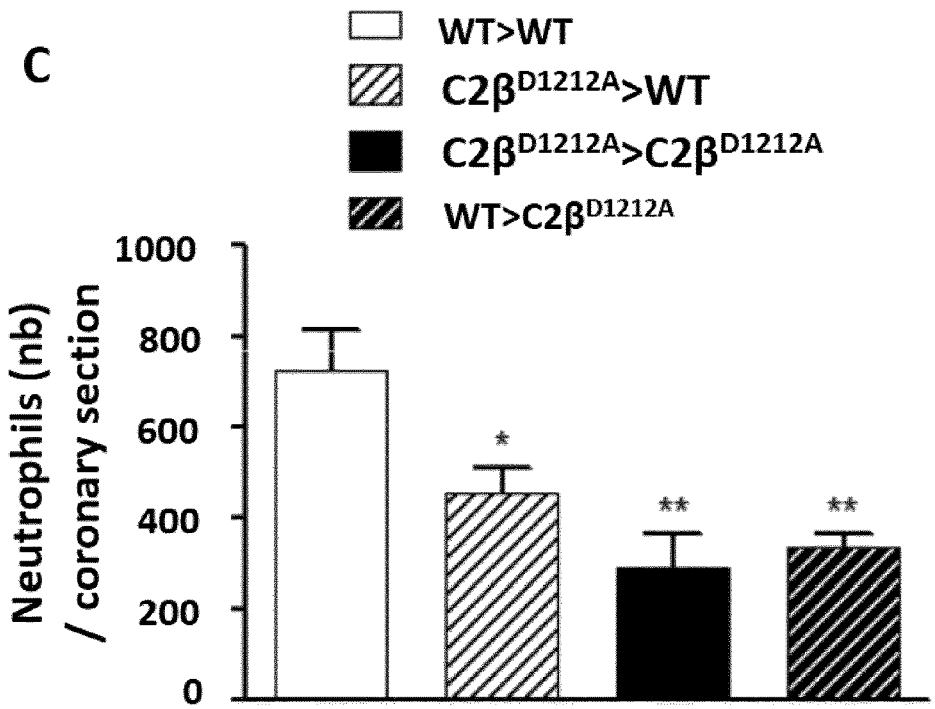

FIG. 3 Role of endothelial versus hematopoietic PI3K-C2β in its neuroprotective effects. (A) Inhibition of endothelial PI3KC2β reduces cerebral infarction—Graph quantification of infarct volume measurements in bone marrow (BM) chimeric mice one day after tMCAO (n=13-16 mice per group) P<0.01; *P<0.001, unpaired t-test. WT>WT: transplantation of WT BM into WT hosts; C2β$^{D1212A/D1212A}$>WT: transplantation of PI3K-C2β KI BM into WT hosts; C2β$^{D1212A/D1212A}$>C2β$^{D1212A/D1212A}$: transplantation of PI3K-C2β KI BM into PI3K-C2β KI hosts; WT>C2β$^{D1212A/D1212A}$: transplantation of WT BM into PI3K-C2β KI hosts. A stronger protection was observed when WT BM was transplanted into PI3K-C2β KI hosts (WT>KI) suggesting that the inhibition of non hematopoietic PI3K-C2β (likely endothelial) was critical to protect from ischemic stroke lesions. (B) Inhibition of endothelial PI3KC2β reduces edema—Edema volume in chimeric mice 24 hours after tMCAO (n=13 mice per group). **P<0.01 vs WT controls; Unpaired t-test. (C) Inhibition of endothelial PI3KC2β reduces neutrophils infiltration—graph quantification for neutrophils infiltration in the ischemic hemisphere in the indicated groups 24 hours after tMCAO (WT>WT n=6; KI>WT n=4; KI>KI n=7; WT>KI n=5; Mann Whitney test).

Figure 4A:
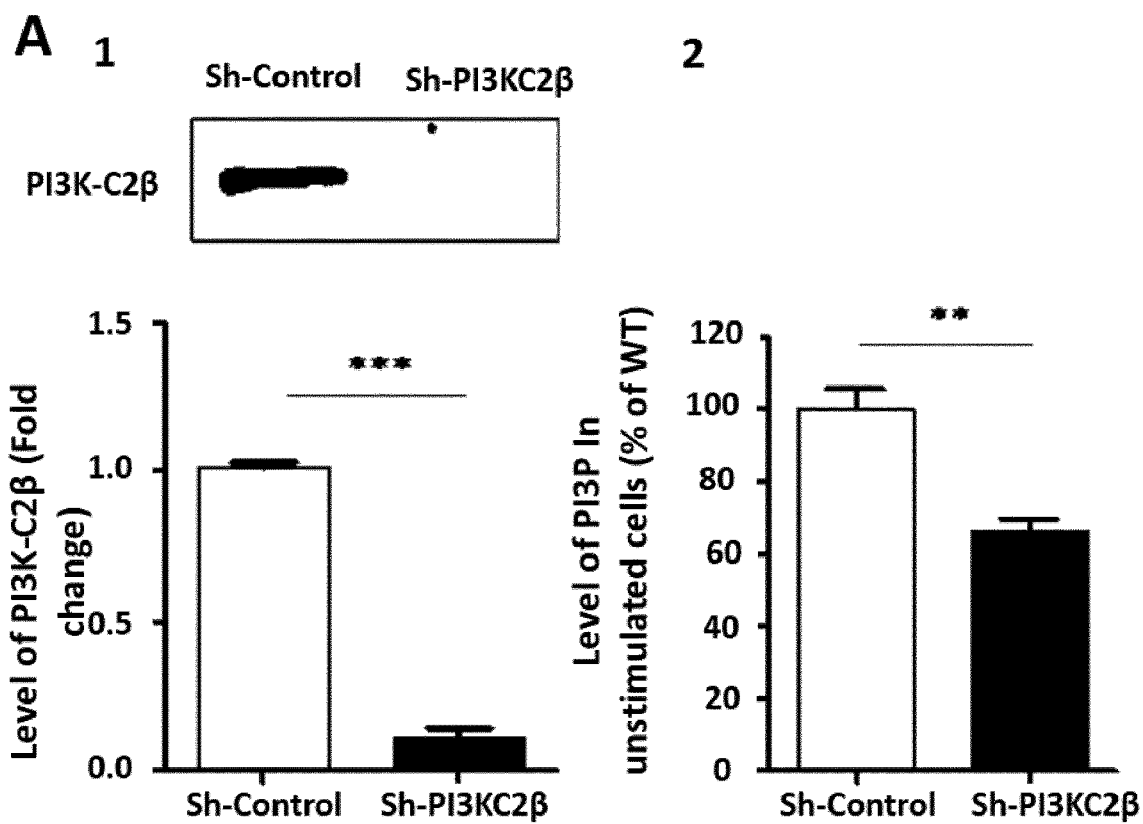
Figure 4B:
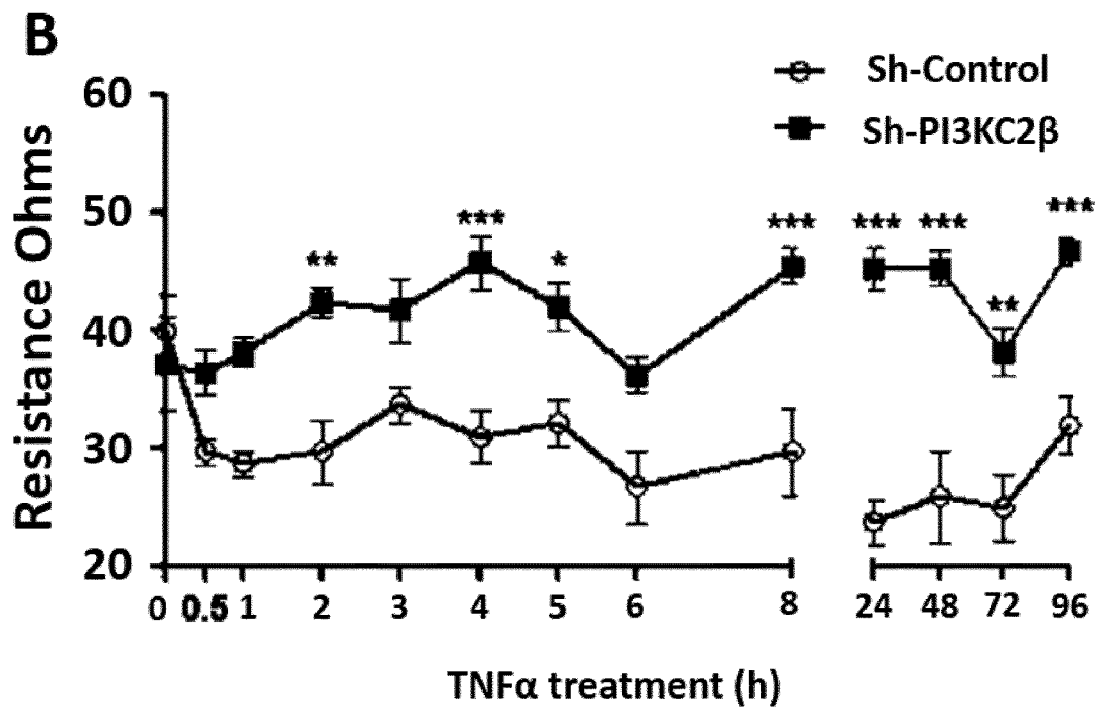
Figure 4C:
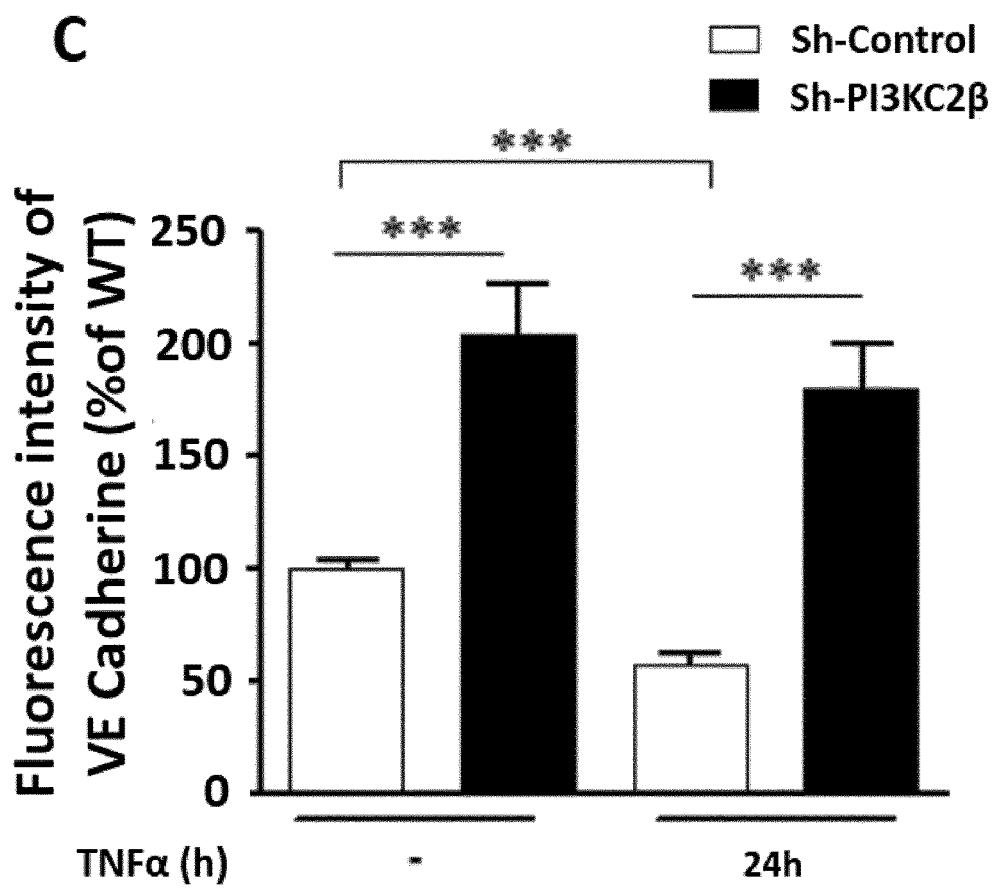

FIG. 4 Impact of PI3K-C2β knock-down on endothelial (hCMEC/D3 cells) monolayer permeability. (A) PI3K-C2β is critical for the regulation of PI3P level in endothelial cells (1) Lysates from human brain capillary endothelial cells (hCMEC/D3) transduced with shRNA control (Sh-control) or shRNA directed against PI3K-C2β (Sh-PI3KC2β) were submitted to immunoblotting with anti-PI3KC2β antibody as indicated. Quantifications by densitometric analysis of the western blots are shown and are mean±SEM of 6 independent experiments. (2) Graph quantification of PI3P mass assay with hCMEC control (sh-Control) or PI3K-C2β knocked-down (sh-PI3K-C2β) cells showed that PI3KC2β was responsible of PI3P production. (B) PI3K-C2β knocked-down reduces inflammation-associated endothelial permeability—Confluent endothelial hCMEC cells transduced with shRNA control (Sh-control) or shRNA directed against PI3K-C2β (Sh-PI3KC2p) were cultured on transwell and stimulated with TNFα (25 ng/ml) over the time. The transendothelial electrical resistance (TEER) was measured with a voltohmeter Millicell ERS-2. Data are shown as mean±SEM (n=3). *P<0.001; P<0.01; *P<0.05, significance differences from control. (C) PI3K-C2β knocked-down maintains VE-cadherin to endothelial cell (EC) junctions in response to TNFα—Graph quantification of VE-cadherin immunoreactivities undertaken in hCMEC control (sh-Control) or knocked-down for PI3K-C2β (sh-PI3K-C2β) under basal conditions and after activation by TNFα (25 ng/ml) during 24 hours. Quantification further confirmed disrupted EC junctions in Sh-Control hCMEC cells 24 h after TNFα stimulation whereas VE-cadherin accumulated in PI3K-C2β knocked-down EC (sh-PI3K-C2β). Data represent mean±SEM (n=5), *P<0.001; P<0.01; *P<0.05.

EXAMPLE

Methods

Mice

PI3K-C2β$^{D1212A/D1212A}$ knock-in mice and wild-type littermates bred on a C57BL/6 background were generously provided by B. Vanhaesebroeck (Alliouachene, S et al. *Cell Reports* 13 (9), 2015). All experiments were performed on 8- to 12-weeks-old mice, unless otherwise specified, and housed in Anexplo vivarium (US006/Regional center of functional exploration and experimental resources, Inserm/Université Paul Sabatier, Toulouse, France). Animals' procedure were approved by the institutional animal care and use committee (CEEA-122 2014-54) and conduced in accordance with the guidelines of the national institute of health.

Generation of Bone Marrow Chimeric Mice

The recipient mice were irradiated to the non-invasive exploration platform located at the Nuclear Medicine Department of the Rangueil Hospital (Biobeam Biological Irradiator 8000). The animals received a single dose of 9 Gray (Gy) for 6 min and their immune system rescued by bone marrow transplantation from either WT or PI3K-C2β KI donors after 24 h in ventilated cages with drinking water supplemented with 10% antibiotics Baytril (Bayer). The tMCAO surgery was performed approximately 4 weeks later.

tMCAO Versus Thromboembolic Stroke Mice Model

To investigate the functional role of class II PI3K-C2β in reperfusion injury induced by ischemic stroke we use the mechanical mouse model of tMCAO and the model of thromboembolic stroke. These two models provide powerful experimental approaches for translational stroke research and are representative of two different clinical situations. The first model results in prompt recirculation, mimicking cerebrovascular surgery or interventional thrombectomy, whereas the second mimics the cellular and molecular mechanisms of thrombosis and thrombolysis with tissue-type plasminogen activator (rt-PA), resulting in the gradual restoration of the recirculation. These two models provide powerful experimental approaches for translational stroke research and are representative of the two different clinical situations.

Transient Middle Cerebral Artery Occlusion (tMCAO)

Mice were anesthetized with 3% isoflurane in a mixture of 70% N2O/30% O2 for cerebral focal ischemia-reperfusion induction by tMCAO according to the established procedure Braeuninger et al., Methods Mol Biol. 2012; 788:29-42). After midline neck incision, the internal carotid artery was occluded with an 18-mm length of 4-0 nylon monofilament with a flame-rounded tip to occlude the origin of the Middle Cerebral Artery (MCA). After 1 h occlusion, mice were reanesthetized, the suture and ligatures were removed to initiate reperfusion for 24 h. Successful induction of focal ischemia was confirmed by contralateral hemiparesis. Exclusion criteria were excessive bleeding or death within 24 h after tMCAO.

Thromboembolic Stroke

Mice were anesthetized with isoflurane (4-5% for induction, 1-2% thereafter) in a 70% N2O/30% O2 gas mixture. Thereafter, they are placed in a stereotaxic frame, the skin between the right eye and the right ear is incised, and the temporal muscle is retracted. A small craniotomy is performed, the dura is excised, and the middle cerebral artery (MCA) exposed. The pipette (glass micro-pipette, tip size 30-50 μm) is introduced into the lumen of the artery and 1 μL of murine α-thrombin (Haematologic Technologies Inc., Stago BNL, NL) is injected to induce in situ clot formation (Orset C, Stroke. 2007; 38(10):2771-2778). The pipette is not removed for 10 min after the injection of thrombin to allow the clot stabilization. The rectal temperature is maintained at 37±0.5° C. throughout the surgical procedure using a feedback-regulated heating system. Cerebral blood flow velocity (CBFv) is used as an occlusion index (blood flow is reduced by up to 60% of baseline) and is monitored using a laser Doppler within the MCA territory on the dorsal face of the skull over 60 min. These experiments were performed in the Experimental Stroke Research Platform (ESRP, Caen, France).

In Vivo Brain Imaging In vivo brain imaging is performed in the Biomedical Imaging Platform (Cyceron, Caen, France) using a 7t MRI (Brucker, pharmascan) on anesthetized mice (2% isoflurane in a 70% nitrous oxide and 30% oxygen mixture), 24 h post-occlusion. For this purpose, a set of sequences in the axial plan including time-of-flight angiography, T2-weighted (T2W), and T2*-weighted (T2*W) imaging will be performed. These sequences allow the assessment of arterial recanalization, ischemic infarction, and brain hemorrhages, respectively. Images are then post-processed using imageJ software for ischemic calculation and angiographic score measurements.

Evans Blue Extravasation

The integrity of the blood brain barrier (BBB) was assessed by measuring extravasation of Evans blue dye into the brain parenchyma. A 2% solution of Evans blue in saline was injected intravenously at 4 mL/kg 1 h after induction of tMCAO. Twenty four hours later, mice were anesthetized with isoflurane and perfused with saline through the left cardiac ventricle until infusion fluid was colorless. Mice were sacrificed, brains were removed and 2-mm coronal sections were sliced for photography.

Immunohistochemistry

Front and rear portions of each brain that were postfixed for 48 hours at 4° C. in 10% neutral buffered formalin (Sigma), embedded in paraffin, and sectioned at a thickness of 10 μm. Tissue sections were mounted on pretreated slides and deparaffinized in xylene. Hematoxylin-and-eosin (HE) staining was performed on selected sections from each brain to assess the degree of leukocyte infiltration.

RNA Extraction and Reverse Transcription

Tissues were homogenized and total RNA were extracted in Trizol reagent (Life Technologies, Gaithersburg, MD, U.S.A.) according to the manufacturer's suggested protocol. Total RNA concentration was determined from spectrophotometric optical density measurement (260 and 280 nm). Reverse transcriptase reactions were then carried out using the RNA PCR Core Kit (GeneAmp RNA PCR Core kit, ThermoFischer Scientific). Experiments were realized according to the manufacturer's suggested protocol and were carried out in a DNA Thermal Cycler 480 (Perkin Elmer, Branchburg, NJ, U.S.A.). The cDNA was then stored at −20° C.

The cDNA sequences for RPS29 (ribosomal protein small subunit 29), interleukin-1β (IL-1β), IL-6 and tumor necrosis factor-α (TNF-α) were obtained from GeneBank. The primer and probe sequences used are reported in Table 1. Real-time PCR was performed using the TaqMan Universal PCR Master Mix. All samples were run in duplicate and the output level reported as the average of the two duplicate. Amplification conditions were performed using ABI PRISM 7700 sequence detection system (PE Applied Biosystems). The threshold cycle, which represents the PCR cycle at which an increase in reporter fluorescence above background is first detected, was determined by the software, based on the standard curves.

Using the formula provided by the manufacturer (PE Applied Biosystems) and described by Wang et al. (Wang et al. *Journal of Neuroscience Research,* 2000; 59: 238-246, Wang et al. *J Cereb Blood Flow Metab,* 2000; 20: 15-20), the values were extrapolated to calculate the relative number of mRNA copies as compared with RPS29 levels as control. The data are presented as the mean±SD. ANOVA followed by Tukey post hoc analysis was used to evaluate differences between time points. Student's t-tests were used to evaluate differences between left and right hemispheres.

Cell Culture

Immortalized human brain capillary endothelial cells (hCMEC/D3 cell line), which retain the characteristics of the cerebral circulation (Weksler, B. B. et al. *The FASEB Journal,* 2005, 19, n° 13: 1872-74), were cultured in rat tail collagen I (Cultrex, Trevigen, France) coated plates (1.5 mg/mL) in medium consisting of EndoGRO medium (Merck Millipore) supplemented with a dedicated supplement (EndoGRO MV Supplement Kit, Merck Millipore), 1 ng/mL basal Fibroblast Growth Factor (Sigma-Aldrich) and 1% penicillin—Streptomycin (Invitrogen). Cells were cultured in an incubator at 37° C. with 5% $CO_2$ and saturated humidity. From these cells, a batch having integrated a vector by lentiviral transduction was created. HCMEC/D3 pLKO-ShRNA PI3KC2β (shRNA-PI3K-C2β) cells having integrated a shRNA directed against PI3K-C2β. For the cells transduced by the shRNA-PI3K-C2β or shRNA-control lentiviruses the medium was supplemented with 3 μg/mL puromycin. The cells were passed twice a week with Trypsin/EDTA (Sigma-Aldrich) or accutase (BD Pharmingen). The cells were counted using a cell counter (Z1 coulter particle counter Beckman Coulter Brea USA).

Trans-endothelial electrical resistance (TEER) For trans-endothelial electrical resistance hCMEC/D3 were seeded on type I collagen pre-coated Transwell-Clear filters (Costar, Corning Incorporation). Assay medium was changed after 4 and 7 days and transport assays were performed when cells form monolayers (7-10 days after seeding). Culture systems on inserts were exposed to treatment (hrTNFα at 25 ng/ml), and TEER were measured using an epithelial volt-ohmmeter (Millicell). The resistance of ECM-coated inserts was used as control. The values obtained were plotted on GraphPad software and checked for significance.

Western Blot Analysis

Proteins were extracted from tissues in lysis buffer containing 150 mM NaCl, 20 mM Tris.HCl pH7.4, 1% Triton X-100, 0.2% SDS, 4 mM EDTA, 10 µg/ml leupeptin, 10 µg/ml aprotinin, 1 mM Na3VO4, 1 mM PMSF. The homogenate was cleared by centrifugation at 411 C for 20 min at 13,000 g and the supernatant fraction recovered. Protein concentration was determined by colorimetric assay (BCA, Pierce). Homogenates were resolved by SDS-PAGE, transferred to nitrocellulose membranes and probed with antibodies to PI3K-C2β (1:1000) from BD Biosciences (#611342) overnight at 4° C. Antigen-specific binding of antibodies was visualized by ECL.

Immunofluorescence

Cells were seeded at $2.5 \times 10^4$ cells·cm$^{-2}$ in collagen I-coated glass coverslip in 24 well plates. After snap wash in PBS, cells were fixed in 4% formaldehyde and permeabilized with 0.1% Triton X-100. Cells were blocked in PBS with 1% BSA fatty acid-free 1 h and incubated with VE-Cadherin primary antibody (#555661, BD Pharmingen) in blocking solution 2 h at RT in humid chamber. After washes, lamellae are incubated with the appropriate fluorescent secondary antibody and DAPI to evaluate cell number. Coverslips were mounted on glass slides with Mowiol mounting solution. Confocal images were captured with a LSM780 operated with Zen software (Carl Zeiss). Profiling of fluorescence intensity was carried out with ImageJ (National Institute of Health, Bethesda, MA, USA).

Mass Assay

PI3P levels were quantified by a mass assay as previously described (Chicanne, G. et al. *Biochemical Journal.* 2012, 447, n° 1: 17-23). Preparation of cell extract for mass assay was as follows. After removing media, cells were immediately scraped off and recovered in ice-cold 1 M HCl, followed by centrifugation at 2000 rpm at 4° C. and snap-freezing of the cell pellet. Samples were stored at −80° C. before processing for PI3P mass assay.

Statistical Analysis

All data are shown as mean+/−S.E.M. The statistical significance of differences between means was calculated by one-way anova, two-way anova or t-test analysis, as appropriate. Statistical significance was assumed at p<0.05 and indicated as *p<0.05, p<0.01, *p<0.001 realize using Prism Software (GraphPad, version 5).

Results

The results are depicted in FIGS. 1-4.

Firstly, the results show that genetic inhibition of PI3K-C2β reduces the cerebral infarction in two ischemia/reperfusion (I/R) models and improves neurological outcome. C2β$^{D1212A/D1212A}$ mice displayed a significantly improved outcome compared to WT mice resulting in a significant increase in survival, a better overall neurologic function 24 hours after tMCAO (Bederson score: mean, 2.82 for WT vs 2.04 for C2β$^{D1212A/D1212A}$; P<0.05) and an improved motor function and coordination (grip test score: mean, 2.26 for wild-type vs 3.07 for C2β$^{D1212A/D1212A}$; P<0.05) (FIG. 1). Collectively, these data demonstrate that the marked reduction of infarct volume in C2β$^{D1212A/D1212A}$ mice was functionally relevant.

Genetic inhibition of PI3K-C2β stabilizes the blood-brain barrier (BBB after ischemic stroke and reduces inflammation. In the thromboembolic stroke model, ultrasensitive molecular MRI of cerebrovascular inflammatory molecules expressed by endothelial cells, such as adhesion molecule P-selectin, was used to evaluate the degree of brain inflammation in vivo. Antibody-based microsized particles of iron oxide (MPIOs) targeting P-Selectin were injected intravenously in mice 24 h after induction of acute thrombosis in the MCA. MRI was acquired 20 min after intravenous administration of targeted MPIOs. Absence of PI3KC2β activity (C2βD1212A/D1212A mice) efficiently protected from endothelial P-Selectin expression compared to WT mice (2.26% vs 5.18%) indicating a decrease of endovascular inflammation (FIG. 2). The results also show that inhibition of endothelial PI3KC2β reduces cerebral infarction, edema and neutrophils infiltration (FIG. 3). In human cerebral microvascular endothelial hCMEC/D3 cells, the results show that PI3K-C2β is critical for the regulation of PI3P level and PI3K-C2β knocked-down reduces inflammation associated endothelial permeability. PI3K-C2β knocked-down maintains VE-cadherin to endothelial cell (EC) junctions in response to TNFα (FIG. 4)

Altogether these results highlight the involvement of PI3K-C2β in infarct generation and CNS inflammation in two different models of stroke and demonstrate that inhibition of this lipid kinase is beneficial in acute ischemic stroke.

REFERENCES

Throughout this application, various references describe the state of the art to which this invention pertains. The disclosures of these references are hereby incorporated by reference into the present disclosure.

The invention claimed is:

1. A method for screening a plurality of test substances useful for the treatment of an ischemic condition in a patient in need thereof comprising
   (i) providing a PI3KC2β protein;
   (ii) contacting the PI3KC2β protein with a test substance;
   (iii) selecting a test substance that decreases the kinase activity of PI3KC2β in comparison to a negative control as useful for the treatment of an ischemic condition; and
   (iv) providing the test substance selected in (iii) in a pharmaceutical composition in an amount effective for treatment of an ischemic condition.

2. The method of claim 1, wherein the test substance is a small organic molecule.

3. The method of claim 1, wherein the pharmaceutical composition further comprises a thrombolytic agent.

4. The method of claim 3, wherein the thrombolytic agent is tissue-type plasminogen activator (t-PA).

5. The method of claim 1, wherein the amount effective for treatment of an ischemic condition is an amount effective for preservation of vascular endothelial cell barrier integrity.

* * * * *